United States Patent [19]

Baglioni

[11] Patent Number: 4,618,612
[45] Date of Patent: Oct. 21, 1986

[54] ESTER DERIVATIVES OF 7-(ω-OXYALKYL) THEOPHYLLINE AND THEIR PHARMACEUTICAL ACTIVITY

[75] Inventor: Alessandro Baglioni, Rome, Italy

[73] Assignee: Medosan Industrie Biochimiche Riunite S.p.A., Albano Laziale, Italy

[21] Appl. No.: 618,661

[22] Filed: Jun. 8, 1984

[30] Foreign Application Priority Data

Jun. 10, 1983 [IT] Italy .............................. 48471 A/83

[51] Int. Cl.⁴ ..................... A61K 31/52; C07D 473/08
[52] U.S. Cl. ..................................... 514/265; 544/267
[58] Field of Search ...................... 544/267, 269, 270; 548/533, 562, 563, 537; 424/253; 514/263, 264, 265

[56] References Cited

U.S. PATENT DOCUMENTS

| | | | |
|---|---|---|---|
| 2,517,410 | 8/1950 | Papesch | 544/267 |
| 3,652,586 | 3/1972 | Denss et al. | 548/563 |
| 3,673,212 | 6/1972 | Denss et al. | 548/563 |
| 3,752,826 | 8/1973 | Carson | 548/527 |
| 3,892,769 | 7/1975 | Shen et al. | 548/563 |
| 4,161,609 | 7/1979 | Cramer | 560/215 |
| 4,187,230 | 2/1980 | Wiegland et al. | 548/562 |
| 4,275,064 | 6/1981 | Budor et al. | 424/253 |

FOREIGN PATENT DOCUMENTS 535232  5/1973  Switzerland .

OTHER PUBLICATIONS

J. Murdoch Ritchie "Central Nervous System Stimulants, II. The Xanthines" The Pharmacological Basis of Therapeutics, third edition, Louis S. Goodman and Alfred Gilman, pp. 354–366 (1965).
Serchi, G. et al., Il Farmaco, Ed. Sci. vol. 12, 594–597 (1957).
Gorczyca, M.: Chem. Abstracts, 59 13977(g) (1963).
Merz, K. et al.: Chem. Abstracts 55 1626(g) (1961).

*Primary Examiner*—Veronica P. Hoke
*Attorney, Agent, or Firm*—Cushman, Darby & Cushman

[57] ABSTRACT

New ester derivatives of 7-(ω-oxyalkyl theophylline with the general formula

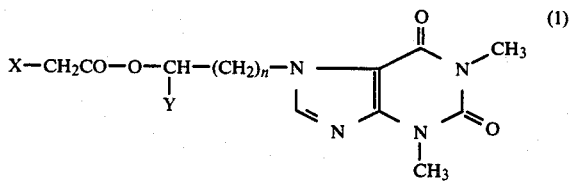

where X is an aroylpyrrole group, a pyrrylphenyl group, or an aroylpyrrol acetamide group and Y is hydrogen, methyl or a theophylline radical, show antiplatelet aggregation, antinflammatory and broncholytic activity, accompanied by low toxicity.

15 Claims, No Drawings

ESTER DERIVATIVES OF 7-(ω-OXYALKYL) THEOPHYLLINE AND THEIR PHARMACEUTICAL ACTIVITY

BACKGROUND OF THE INVENTION

1. Field of the Invention

The present invention concerns ester derivatives of 7-(ω-oxyalkyl)theophylline substituted with aroylpyrrolacetic, pyrrylphenylacetic and aroylpyrrolacetamidacetic acids. The anti-platelet aggregation, antinflammatory and broncholytic activity of these esters has been demonstrated.

2. Prior Art

Theophylline is a known alkaloid with analeptic activity which is used therapeutically in its unsubstituted or derivative form as a diuretic, cardiac stimulant and smooth muscle relaxer. However, it shows relatively high toxicity.

1-methyl-5-p-methylbenzoylpyrrol-2-acetic acid, also known as tolmetin, is a known antinflammatory agent used in therapy as its sodium salt (see U.S. patent application Ser. No. 656,074, 26 July 1967, and now abandoned J. R. Carson), with the following formula:

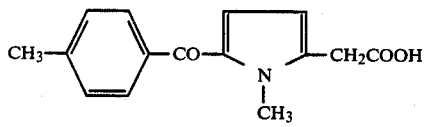

4-(1-pyrryl)-phenylacetic acid is also a known antinflammatory agent, described in Swiss Pat. No. 535232 of 7 August 1967, with the following formula:

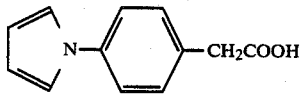

Some antinflammatory drugs have been demonstrated to show anti-platelet aggregation as well (for example, dithazol see Rynbrandt at al., *J.Med. Chem.*, 24, 1507 (1981)).

SUMMARY OF THE INVENTION

It has now been discovered that the new compounds according to the invention, 7-(ω-oxyalkyl) substituted theophylline esters, show fundamental therapeutic activity as anti-platelet aggregation agents, as well as broncholytic and associated antinflammatory activity.

These activities have surprisingly been shown to be accompanied by an extremely high toxicity value, that is, by extraordinarily low toxicity, so that these compounds have a very high therapeutic index. It had not been foreseen that compounds derived from theophylline would show anti-platelet aggregation activity, while at the same time showing toxicity several orders of magnitude lower than that of their components.

The esters according to the invention are represented by the general formula (1):

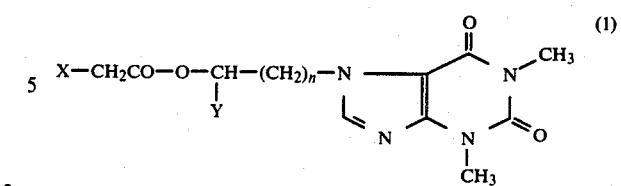

in which X represents:

(a) an aroylpyrrole group of general formula

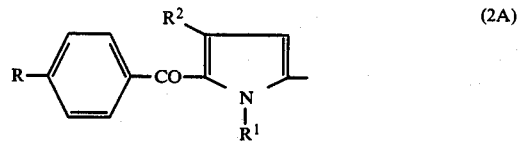

where R is a hydrogen, chlorine, methyl or ethyl, $R^1$ is a methyl group, and $R^2$ is hydrogen or methyl;

(b) a pyrrylphenyl group of general formula

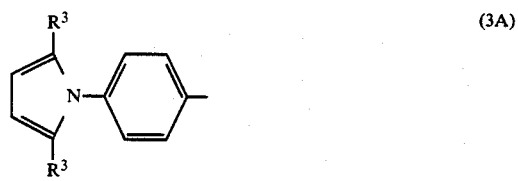

where $R^3$ is a hydrogen atom or a methyl group;

(c) an aroylpyrrolacetamide group of general formula

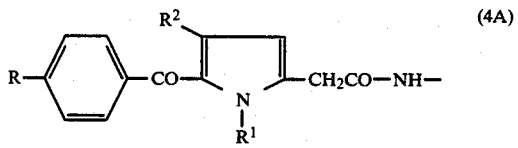

in which R, $R^1$ and $R^2$ have the same meaning as in (a); and Y represents a hydrogen atom or the following radical

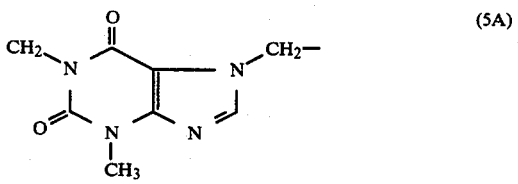

and n represents a number between 1 and 5.

All of these compounds possess antinflammatory properties due to the aroylpyrrolacetic component typical of tolmetin, or to the pryrrylphenylacetic portion typical of 4-(1-pyrryl)-phenylacetic acid.

In addition to the pharmacological properties mentioned above, the compounds with formula (1) show pronounced anti-platelet aggregation activity as their fundamental activity, as well as extraordinarily low toxicity.

DESCRIPTION OF THE PREFERRED REALIZATIONS

The esters with formula (1) were prepared by reaction of the acids with general formulae (2) (3), and (4)

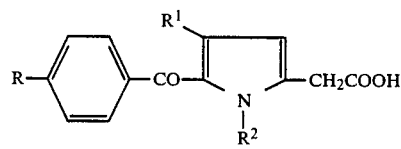
(2)

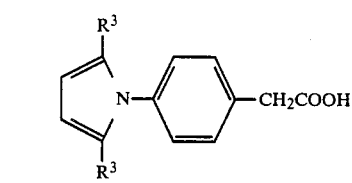
(3)

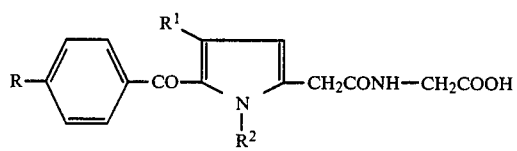
(4)

in which R, $R^1$, $R^2$ and $R^3$ have the same meaning as indicated above, with an approximately stoichiometric amount of an alcohol with general formula (5)

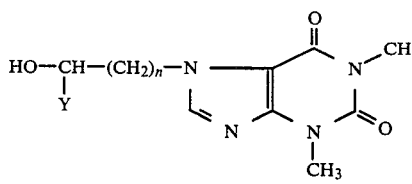
(5)

in which Y and n have the same meaning as indicated above, preferably in the presence of an activated derivative of a substituted acetic acid with general formula

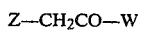
Z—CH$_2$CO—W in which W is an activating group which can promote formation of an ester bond with the alcohols previously indicated above, Z is a radical chosen from the following three formulae

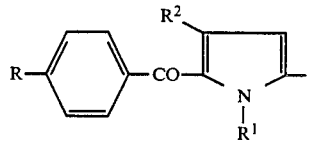

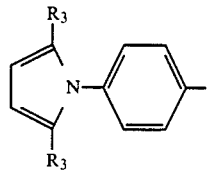

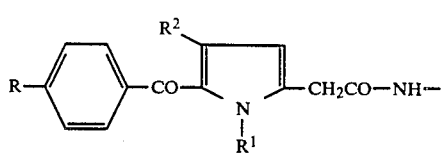

in which R, $R^1$, $R^2$ and $R^3$ have the same meaning as indicated above.

The quantity of alcohol (5) used varies from 1 to 1.5 times the equivalent amount of acid (2), (3) or (4), preferably 1.2 equivalents.

The condensing agent may consist of N,N'-dicyclohexylcarbodiimide or of a mixture with p-tolyenesulfonic acid or with 4-dimethylaminopyridine in catalytic quantities, or alternatively, of from 1 to 1.5 equivalents (preferably 1.2 equivalents) of N,N'-carbonyldiimide, with or without ethyl magnesium. Other dehydrating agents or the cation of the acid chlorides of (2), (3) or (4) or the corresponding alcohols (5) give the esters (1) analogously. They may also be obtained by the esterification of the acids (2), (3) or (4) with the alcohols (5) in the presence of inorganic or organic acids as catalysts or by using catalytic quantities of an inorganic or organic base in a suitable solvent, for example gaseous hydrochloric acid, concentrated sulfuric acid, p-toluenesulfonic acid, or with sodium hydroxide, ethyl sodium, ethyl magnesium, Triton B, pyridine, piperidine and derivatives in polar and apolar solvents as required.

The esters (1) may also be prepared by transesterification.

The reaction for preparing the esters is shown schematically by the condensation of 1-methyl-5-p-methylbenzoylpyrrol-2-acetic acid and 7-(2-oxyethyl)theophylline as a general example, giving rise to the formation of the 1-methyl-5-p-methylbenzoylpyrrol-2-acetate of 7-(2-oxethyl)-theophylline:

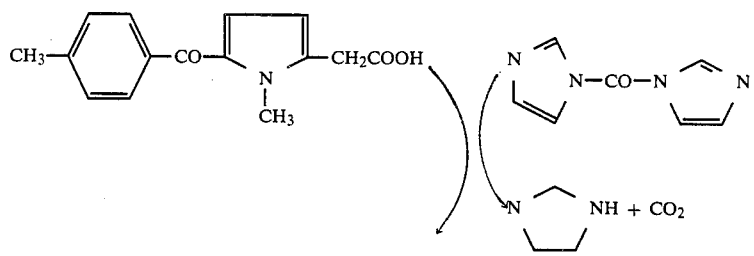

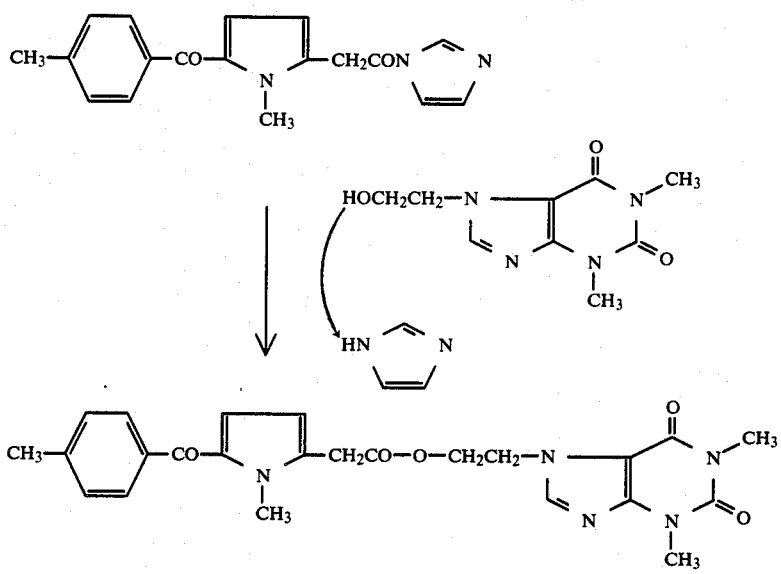

The reaction is generally run in non-polar medium, although water-dioxane or water-tetrahydrofuran mixtures may also be used when N,N'-dicyclohexyl-carbodiimide is used as condensing agent with or without catalyst. The solvents used most often are: tetrahydrofuran, dichloromethane, dichloroethane dimethylsulfoxide, dioxane, N,N'-dimethylformamide.

The best yields are achieved with anhydrous solvents; they range from 60% to 90%, with an average value of 75%. The reaction is run at a temperature in the 60°–90° range, with optimal results at a temperature of approximately 80° C.

The reaction is carried out with vigorous stirring, under nitrogen or other inert gas if necessary, while adding the reagents gradually. The reaction goes to completion in a period of 2-8 hours of heating at 60°–90° C. and one of 12-24 hours of rest at room temperature, as a function of the alcohol and acid used as reagents.

Work-up of the reaction mixtures is performed in the usual fashion, using normal separation techniques like filtration or column chromatography on silica gel, activated or partially deactivated alumina, or other inert adsorbent material.

The compounds (1) were identified from their I.R. spectra. Elemental analysis was performed on all compounds, and the resulting analytical data were within ±0.3% of the theoretical values.

EXAMPLE 1

General esterification method

1-Methyl-5-p-methylbenzoylpyrrol-2-acetate of 7-(2-oxyethyl)theophylline (1), $Y=H$; $n=1$ and $X=(2)$, where $R=R^1=CH_3$ and $R^2=H$ A solution of 2.57 g of 1-methyl-5-p-methylbenzoyl-pyrrol-2-acetic acid (0.01 mole) in 100 ml of anhydrous tetrahydrofuran was treated under vigorous stirring with 1.9 g of N,N'-carbodiimidazol (0.012 mole) in 50 ml of anhydrous tetrahydrofuran. The mixture was stirred for 30 minutes, and then treated over the course of an hour with 2.7 g of 7-(2-oxyethyl)theophylline (0.012 mole) in 50 ml of anhydrous tetrahydrofuran. The resulting mixture was then heated at reflux for 3 hours. The resulting clear solution was then stirred for two more days and evaporated to dryness, giving a yellow oil which was dissolved in 250 ml of ethyl acetate and placed in a separatory funnel. The organic solution was first washed with 20% NaOH, and then with water until neutral. It was then dried over anhydrous sodium sulfate for 12 hours. Evaporation of the solvent offorded a pale yellow oil which solidified upon treatment with a small amount of ethyl ether. The solid was isolated by filtration to afford 2.3 g of product which was crystallized from methanol to give 1.9 g of 1-methyl-5-p-methylbenzoylpyrrol-2-acetate of 7-(2-oxyethyl)theophylline, m.p.=150°–155° C.

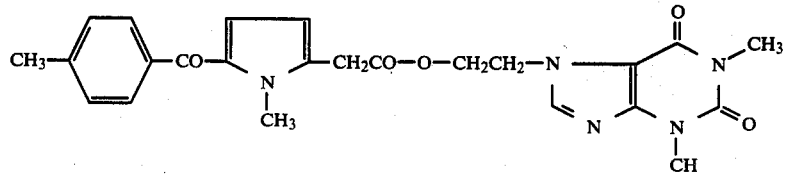

PREPARATION EXAMPLE

The compounds which are the object of this invention were prepared according to the method reported below for the esterification of 1-methyl-5-p-methylbenzorylpyrrol-2-acetic acid (2), $R=R^2=CH_3$—; $R^1=H$ with 7-(2-oxyethyl)theophylline (5), $R=H$; $n=1$:

Formula: $C_{24}H_{25}N_5O_5$
Molecular weight: 463,48
Melting point: 150°–155° C.
Yield: 41%
Solubility: Soluble in common organic solvents Analysis: for $C_{24}H_{25}H_5C_5$ calc. % C: 62,19, H: 5,44, N: 15,11, found % C: 62.42, H: 5,16, N: 14,95.

I.R. spectrum (nujol) 1750 cm$^{-1}$, 1700 cm$^{-1}$ and 1670 cm$^{-1}$ (ester, ketone and amide C=O groups).

EXAMPLE 2

1,4-Dimethyl-5-p-chlorobenzoylpyrrol-2-acetate of 7-(2-oxyethyl)theophylline (1) with Y=H; n=1 and X=(2) where R=Cl and $R^1=R^2=CH_3$ This compound is prepared starting from 1,4-dimethyl-5-p-chlorobenzoylpyrrol-2-acetic acid (2) with R=Cl and $R^1=R^2=CH_3$ and 7-(2-oxyethyl)theophylline (5) with R=H and n=1, according to the procedure described in example 1.

EXAMPLE 3

1-Methyl-5-p-methylbenzoylpyrrol-2-acetate of 7-(3-oxypropyl)theophylline (1) with Y=H; n=2 and X=(2) where $R=R^1=CH_3$ and $R^2=H$ This compound is prepared starting from 1-methyl-5-p-methylbenzoylpyrrol-2-acetic acid (2) with $R=R^1=CH_3$ and $R^2=H$ and from 7-(3-oxypropyl)theophylline (5) with R=H and n=2, according to the procedure described in example 1.

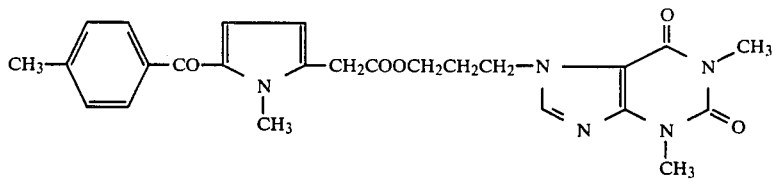

Formula: $C_{25}H_{27}N_5H_5$
Molecular weight: 477,51
Melting point: 125°-128° C.
Yield: 50%

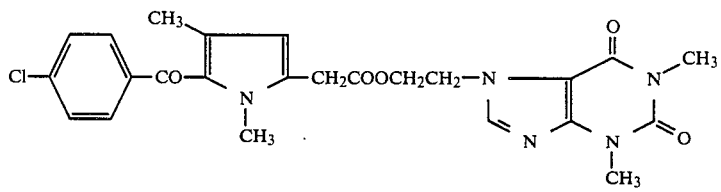

Formula: $C_{24}H_{24}ClN_5O_5$
Melting point: 150°-152° C.
Molecular weight: 497,5
Yield: 48%
Solubility: Soluble in common organic solvents
Analysis: for $C_{24}H_{24}ClH_5O_5$ calc. % C: 57,89, H: 4,82, N: 7,14, Cl: 14.0, found % C: 57,63, H: 4,70, N: 7,33, Cl: 13,9.

Analysis: for $C_{25}H_{27}N_5H_5$ calc. % C: 62,88, H: 5,70, N: 14,67, found % C: 62,69, H: 5,48, N: 14,86.

I.R. spectrum (nujol): 1750 cm$^{-1}$, 1700 cm$^{-1}$ and 1650 cm$^{-1}$ (C=O groups).

The derivatives reported below were prepared analogously:

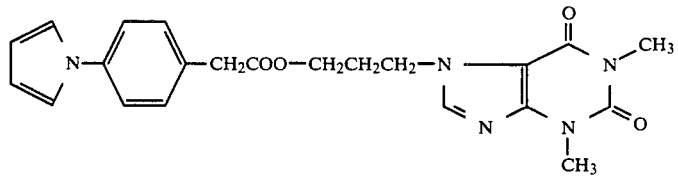

Formula: $C_{22}H_{23}N_5O_4$
Molecular weight: 421,44

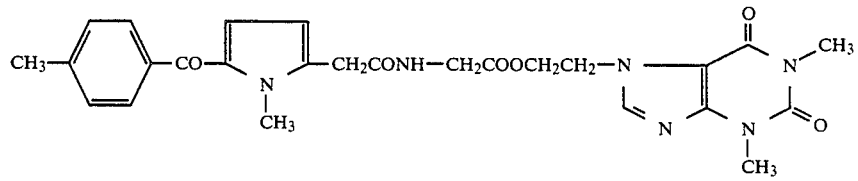

I.R. spectrum (nujol): 1750 cm$^{-1}$, 1710 cm$^{-1}$ and 1670 cm$^{-1}$ (C=O groups).

Formula: $C_{26}H_{28}N_6O_6$
Molecular weight: 520,53

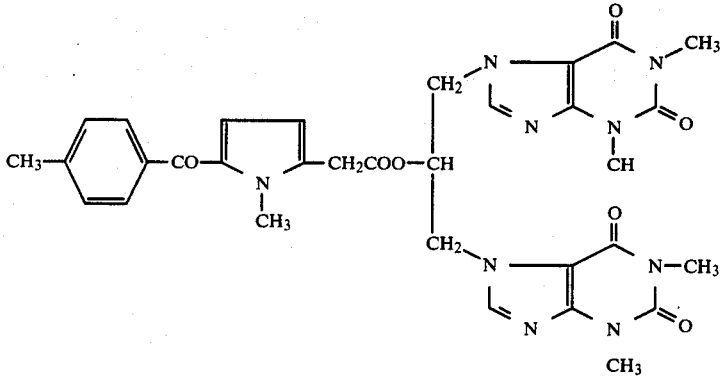

Formula: $C_{32}H_{33}N_9O_7$
Molecular weight: 655

PHARMACOLOGICAL PROPERTIES

The experiments run with aroylpyrrol and pyrrylphenylacetic esters of 7-(ω-oxyalkyl)theophylline show that these compounds have pharmacological properties of therapeutic application in certain pathological conditions.

Preparations (A), (B), (C), (D), (E) and (F) were administered "in vivo" orally and/or parenterally in 0.5% carboxymethylcellulose suspensions in physiological saline at neutral pH. When tested "in vitro", they were finely dispersed in neutral pH physiological saline.

The test compounds showed anti-platelet aggregation activity, plus good antinflammatory and broncholytic action. These pharmacotherapeutic effects were obtained with dosages and administration method which had no significant toxic effects. They also showed excellent gastric tolerance.

Anti-platelet aggregation activity was compared with aspirin; antinflammatory activity with sodium tolmetin; broncholytic activity with theophylline.

ANTI-PLATELET AGGREGATION ACTIVITY IN RATS

This was studied "in vitro" following Born's method (Born G. W. R., Nature, 194, 937 (1962)) and inducing platelet aggregation with ADP.

Platelet-rich plasma was obtained by centrifugation for 10 minutes at 2,000 rpm of 9 parts rat blood to 1 part 3.13% sodium citrate solution. In performing the aggregation test, 0.2 ml of platelet rich plasm was mixed with a 0.9% NaCl solution to which the test substance was added to a final volume of 0.6 ml; the resulting mixture was incubated at 27° C. for 3 minutes. After inducement with ADP, aggregation was measured continuously with an Elvi 840 Aggregometer (Elvi Logos-Milan) to follow its course. The anti-aggregant effects were determined from the difference in the light transmission of the sample with respect to an ADP control.

The theophylline esters in question were compared to aspirin, which is known for its anti-platelet aggregation activity (H. J. Weiss et al., G. Clin. Inv., 47, 2169 (1968); Platelet Aggregation and Drugs, edited by L. Caprino and E. C. Rossi, p. 235, Academic Press (London), 1974).

Table I reports the platelet aggregation inhibition using different doses of the test compounds at a constant ADP concentration. Table II shows the results obtained on varying ADP concentration.

ANTI-PLATELET AGGREGATION ACTIVITY "IN VITRO" ON HUMAN BLOOD SAMPLES: TABLE III AND TABLE IV

Blood samples (20 ml) were obtained by venal puncture of the antecubital fossa using plastic syringes containing trisodium citrate as anticoagulant (final concentration 0.19% w/v). Platelet rich plasma (PRP) was harvested after slow centrifugation at 170 g for 12 min. and 0.2 ml aliquots were dispensed into plastic cuvettes and stored at room temperature throughout the experiment.

Aliquots of 0.2 ml PRP from each sample were treated with ADP, adrenalin, collagen or arachidonate, until the threshold concentrations of these aggregating agents had been reached. The threshold concentration is defined as the minimum whcih will produce irreversible aggregation. Once established, the threshold concentration was used to challenge test samples of each of the 2 test compounds or vehicle (DMSO) which had been incubated for 1 min. at 37 C. in the holding cell of the agregometer, prior to addition of the aggregating agent.

If inhibition was observed with the initial concentration of test compound used, then this concentration was reduced furthereuntil the minimum effective inhibitory concentration was reached. This was reported as the final concentration in the PRP after addition of 2.5–10 ul of test substance. Similarly if the initial concentration of test substance was not effective the concentration was increased, but not beyond a final concentration in PRP of $10^{-3}M$, since at concentrations of this magnitude a compound is not generally considered to be significantly active in vitro.

TABLE I

Anti-platelet aggregation activity "in vitro" of aroylpyrrol and pyrrylphenyl-acetic esters of 7-(ω-oxyalkyl) theophylline: compounds (A), (B) and (C); at constant ADP concentrations

| Inducing agent | compound | dose | % inhibition |
|---|---|---|---|
| ADP 7.08 μmol/l | (A) | 1 /ml | 25 |
| " | " | 2,5 /ml | 100 |
| " | " | 5 /ml | 100 |
| " | (B) | 1 /ml | 20 |
| " | " | 2,5 /ml | 70 |
| " | " | 5 /ml | 90 |
| " | (C) | 1 /ml | 22 |
| " | " | 2,5 /ml | 75 |
| " | " | 5 /ml | 90 |
| " | aspirin | 1 /ml | 15 |
| " | " | 5 /ml | 60 |

TABLE I-continued

Anti-platelet aggregation activity "in vitro" of aroylpyrrol and pyrrylphenyl-acetic esters of 7-(ω-oxyalkyl) theophylline: compounds (A), (B) and (C); at constant ADP concentrations

| Inducing agent | compound | dose | % inhibition |
|---|---|---|---|
| " | " | 10 /ml | 100 |

TABLE II

Anti-platelet aggregation activity "in vitro" of aroylpyrrol and pyrrylphenyl-acetic esters 7-(ω-oxyalkyl) theophylline: compounds (A), (B) and (C); at constant ADP concentration

| Inducing agent | compound | Dose | % Inhibition |
|---|---|---|---|
| ADP 5 μmol/l | (A) | 1 V/ml | 30 |
| " | (B) | " | 25 |
| " | (C) | " | 27 |
| " | (D) | " | 24 |
| " | (E) | " | 29 |
| " | (F) | " | 23 |
| " | aspirin | " | 19 |
| ADP 2 μmol/l | (A) | " | 42 |
| " | (B) | " | 31 |
| " | (C) | " | 36 |
| " | (D) | " | 31 |
| " | (E) | " | 35 |
| " | (F) | " | 32 |
| " | aspirin | " | 29 |

TABLE III

Effect of (A) on Human Platelet Aggregation induced by ADP, Adrenalin, Collagen or Arachidonate (in vitro)

| Aggregation Agent | ADP | Adrenalin | Collagen | Arachidonat |
|---|---|---|---|---|
| Volunteer | Minimim Effective Concentration (Final in PRP) | | | |
| 1. PN ♂ | $1.0 \times 10^{-5}$ M | $1.0 \times 10^{-5}$ M | $1.0 \times 10^{-4}$ M | $1.0 \times 10^{-4}$ M |
| 2. PP ♂ | $1.0 \times 10^{-5}$ M | $1.0 \times 10^{-5}$ M | $5.5 \times 10^{-4}$ M | $1.0 \times 10^{-5}$ M |
| 3. TH ♂ | $1.0 \times 10^{-4}$ M | $1.0 \times 10^{-5}$ M | $7.0 \times 10^{-4}$ M | $2.5 \times 10^{-4}$ m |
| Minimum Effective Concentration range | $1.0 \times 10^{-4}$ M to $1.0 \times 10^{-5}$ M | $1.0 \times 10^{-5}$ M | $7.0 \times 10^{-4}$ M to $1.0 \times 10^{-4}$ M | $2.5 \times 10^{-4}$ M to $1.0 \times 10^{-5}$ M |
| Range | | | | |

TABLE IV

Effect of (C) on Human Platelet Aggregation Induced by ADP, Adrenalin, Collagen or Arachidonate (in vitro)

| Aggregation Agent | ADP | Adrenalin | Collagen | Arachidonate |
|---|---|---|---|---|
| Volunteer | Minimum Effective Concentration (Final in PRP) | | | |
| 1. JC ♂ | $1.0 \times 10^{-4}$ M | $1.0 \times 10^{-4}$ M | $3.5 \times 10^{-4}$ M | $4.0 \times 10^{-4}$ M |
| 2. PP ♂ | $1.0 \times 10^{-4}$ M | $2.5 \times 10^{-7}$ M | $2.5 \times 10^{-4}$ M | $1.0 \times 10^{-5}$ M |
| 3. TH8 ♂ | $2.5 \times 10^{-4}$ M | $1.0 \times 10^{-4}$ M | $1.0 \times 10^{-4}$ M | $1.0 \times 10^{-5}$ M |
| Mimimum Effective Concentration Range | $2.5 \times 10^{-4}$ M to $1.0 \times 10^{-4}$ M | $1.0 \times 10^{-4}$ M to $2.5 \times 10^{-7}$ M | $3.5 \times 10^{-4}$ M to $1.0 \times 10^{-4}$ M | $4.0 \times 10^{-4}$ M to $1.0 \times 10^{-5}$ M |

TABLE V

Antiflammatory activity of aroylpyrrol and pyrrylphenyl-acetic esters of 7(ω-oxyalkyl) theophylline: compounds (A), (B), (C), (D), (E) and (F)

| Compounds | dose mg/kg | % Edema Inhibition | | | | | |
|---|---|---|---|---|---|---|---|
| | | OS | | | I.P. | | |
| | | $3^ah$ | $6^ah$ | $24^ah$ | $3^ah$ | $6^ah$ | $24^ah$ |
| Vehicle | — | 0,0 | 0,0 | 0,0 | 0,0 | 0,0 | 0,0 |
| Na Tolmetin 2H₂O | 10 | 30,5 | 24,0 | 0,0 | 32,0 | 23,0 | 0,0 |
| " | 50 | 49,0 | 52,0 | 0,0 | 48,6 | 53,2 | 0,0 |
| " | 100 | 59,0 | 54,2 | 0,0 | 67,3 | 55,1 | 0,0 |
| (A) | 10 | 34,6 | 22,2 | 0,0 | 35,0 | 26,0 | 0,0 |
| " | 50 | 52,0 | 41,1 | 0,0 | 54,0 | 40,0 | 0,0 |
| " | 100 | 62,0 | 57,3 | 10,0 | 65,0 | 56,1 | 0,0 |
| (B) | 2,5 | 56,4 | 53,0 | 10,0 | 52,0 | 50,0 | 5,1 |
| " | 5 | 66,0 | 60,0 | 12,0 | 65,2 | 60,5 | 10,5 |
| " | 10 | 73,0 | 70,3 | 20,0 | 70,6 | 71,3 | 15,0 |
| (C) | 10 | 40,2 | 34,0 | 0,0 | 38,0 | 36,2 | 0,0 |
| " | 50 | 59,0 | 57,0 | 22,2 | 53,1 | 50,0 | 2,0 |
| " | 100 | 70,0 | 66,1 | 31,0 | 69,5 | 62,0 | 10,0 |
| (D) | 10 | 39,0 | 32,0 | 0,0 | 31,8 | 32,7 | 1,0 |
| " | 50 | 53,1 | 52,0 | 11,6 | 50,1 | 45,9 | 8,6 |
| " | 100 | 66,8 | 64,1 | 16,7 | 67,0 | 65,4 | 9,6 |
| (E) | 10 | 34,0 | 33,8 | 0,0 | 31,8 | 29,0 | 0,0 |
| " | 50 | 54,4 | 49,8 | 10,0 | 56,9 | 54,8 | 12,0 |
| " | 100 | 78,8 | 79,0 | 32,6 | 80,0 | 76,9 | 23,0 |
| (F) | 10 | 23,9 | 24,0 | 0,0 | 43,8 | 34,8 | 0,0 |
| " | 50 | 47,0 | 46,0 | 0,0 | 56,0 | 33,0 | 0,0 |
| " | 100 | 66,0 | 66,0 | 12,0 | 78,6 | 65,6 | 15,8 |

ANTINFLAMMATORY ACTIVITY

This effect was measured with an experimental model reproducing acute inflammation in rats: the carragenin-induced edema test according to C. A. Winter was used (G. Pharmac. Exp. Ther.; 141, 369 (1963)). Table V reports the compounds tested, their concentrations, administration routes and percent edema inhibition as compared to sodium tolmetin.

BRONCHOLYTIC ACTIVITY

The experiments were conducted "in vitro" on guinea pig tracheal chains according to the Akasu method (A. Akasu, Archs. Int. Pharmacodyn., 122, 201 (1959)), using histamine as the bronchial constrictor. The test products were left in contact with the tissue for 3 minutes, and then a certainly spasmogenic dose ($10^{-4}$M) of histamine was administered. The histamine was left in contact with the tissue for 5 minutes. Theophylline was used as the control. The ratio was calculated between the equally active doses of histamine before and after treatment. This value multiplied by 100, considered the percent response, was inversely correlated with the dose of the drug. The results are reported in table VI.

TABLE VI

Antagonist effect of aroylpyrrol and pyrrylphenyl-acetic esters of 7(ω-oxyalkyl) theophylline: compounds (A), (B), (C), (d), (E), (F)

| Compounds | Concentration (g/ml) | No. of experiments | % Response ± S.E. |
|---|---|---|---|
| Theophylline | $1 \times 10^{-5}$ | 5 | 63 ± 9 |
| " | $2 \times 10^{-5}$ | 4 | 30 ± 8 |
| " | $5 \times 10^{-5}$ | 5 | 12 ± 2 |
| (A) | $1 \times 10^{-5}$ | 4 | 61 ± 10 |
| " | $2 \times 10^{-5}$ | 4 | 27 ± 7 |
| " | $5 \times 10^{-5}$ | 4 | 10 ± 3 |
| (B) | $1 \times 10^{-5}$ | 4 | 63 ± 7 |
| " | $2 \times 10^{-5}$ | 4 | 34 ± 8 |
| " | $5 \times 10^{-5}$ | 4 | 9 ± 2 |
| (C) | $1 \times 10^{-5}$ | 4 | 58 ± 9 |
| " | $2 \times 10^{-5}$ | 4 | 26 ± 8 |
| " | $5 \times 10^{-5}$ | 4 | 8 ± 2 |
| (D) | $1 \times 10^{-5}$ | 4 | 59 ± 8 |
| " | $2 \times 10^{-5}$ | 4 | 24 ± 6 |
| " | $5 \times 10^{-5}$ | 4 | 6 ± 5 |
| (E) | $1 \times 10^{-5}$ | 4 | 61 ± 7 |
| " | $2 \times 10^{-5}$ | 4 | 32 ± 6 |
| " | $5 \times 10^{-5}$ | 4 | 10 ± 5 |
| (F) | $1 \times 10^{-5}$ | 5 | 56 ± 9 |
| " | $2 \times 10^{-5}$ | 4 | 32 ± 6 |
| " | $5 \times 10^{-5}$ | 4 | 9 ± 3 |

GASTRIC TOLERANCE

This was studied by conducting tests of ulcerogenic activity in male Wistar rats, weighing 180 g on the average, in groups of 10 animals each. Three doses of each substance were given, and one group of animals was treated with vehicle only in a volume of 10 ml/kg bodyweight. Each dose was given orally for four consecutive days; on the fifth day, the rats were killed and autopsied. The ulcerogenic effect was assessed according to the following scale:

Number of lesions:

(1) each hemorrhage point $\geq 1$ mm was evaluated as 1 lesion
(2) hemorrhage points smaller than 1 mm were counted as follows:
  (a) from 1 to 9:1 lesion
  (b) from 1 to 19:2 lesions
  (c) from 1 to 29:3 lesions Severity of the lesions:
(1) none: 0
(2) gastric mucosa irritation: 1
(3) hemorrahge points <1 mm: 2
(4) hemorrhage points between 1 and 3 mm: 3
(5) hemorrhage points >3 mm: 4
(6) perforations: 5

This scale was used to calculate the following gastric damage index:

$I$ = mean No. of lesions + mean of the severity + $\frac{\% \text{ incidence}}{10}$ The data are reported in table VII.

TABLE VII

Ulcerogenic activity of aroylpyrrol and pyrrylphenyl-acetic esters of 7(ω-oxyalkyl) theophylline: compounds (A), (B), (C)

| Compounds | Dose mg/kg | Mean No. lesions | Mean Severity | % incidence 10 | Gastric Damage index |
|---|---|---|---|---|---|
| Vehicle | — | 1 | 1 | 6 | 8 |
| Na Tolmetin 2H₂O | 50 | 2 | 2 | 7 | 11 + 3 |
| | 100 | 2,5 | 3,5 | 10 | 16 + 8 |
| | 200 | 3 | 4 | 10 | 17 + 9 |
| (A) | 50 | 1 | 2 | 6 | 9 + 1 |
| " | 100 | 2 | 2 | 8 | 12 + 4 |
| " | 200 | 3 | 3 | 8 | 14 + 6 |
| (B) | 2,5 | 1 | 2 | 7 | 10 + 2 |
| " | 5 | 2,5 | 2,5 | 8 | 13 + 5 |
| " | 10 | 3 | 4 | 9 | 16 + 8 |
| (C) | 50 | 1 | 2 | 7 | 10 + 2 |
| " | 100 | 2 | 3 | 9 | 14 + 6 |
| " | 200 | 2 | 4 | 9 | 15 + 7 |

TOXICITY

Acute toxicity of compounds (A), (B), (C), (D), (E), (F) was determined in two animal species: in male Swiss albino mice weighing 26±2 g and in male Wistar rats weighing an average of 130 g, both orally and intraperitoneally.

Table VIII reports the $LD_{50}$ values in mg/kg.

The experimentally determined $LD_{50}$ of tolmetin, as well as the literature values for aspirin and theophilline, are reported as comparisons (Drug Dosage in Laboratory Animals, C. D. Barners and L. G. E. Eltherington; University of California Press, 1973).

TABLE VIII

Acute toxicity of aroylpyrrol and pyrrylphenyl-acetic esters of 7-(ω-oxyalkyl) theophylline: compounds (A), (B), (C), (D), (E), (F)

| Compounds | Animal Species | $LD_{50}$ (mg/kg) OS | $LD_{50}$ (mg/kg) I.P. |
|---|---|---|---|
| (A) | mice | 1,270 | 950 |
| | rats | 1,150 | 800 |
| (B) | mice | 160 | 140 |
| | rats | 150 | 100 |
| (C) | mice | 1,340 | 1,000 |
| | rats | 1,200 | 920 |
| (D) | mice | 1,100 | 780 |
| | rats | 1,000 | 675 |
| (E) | mice | 1,400 | 1,100 |
| | rats | 1,345 | 987 |
| (F) | mice | 1,679 | 1,245 |
| | rats | 1,500 | 1,050 |
| Aspirin | mice | 1,100 | 495 |
| | rats | 1,500 | 500 |
| Na Tolmetin 2H₂O | mice | 899 | 550 |
| | rats | 914 | 612 |
| Theophylline | mice | 200 s.c. | (minimum lethal dose) |
| | rats | 325 s.c. | " |

The data reported in tables I–VIII demonstrate the pharmacotherapeutic effect of the aroylpyrrol and pyrrylphenyl-acetic esters of 7-(ω-oxyalkyl)theophylline, according to this invention, in the range of doses tested and in relationship to the control products. The experimental results, especially regarding the anti-platelet aggregation activity, are even more surprising since no such activity had ever been reported for theophylline or tolmetin.

The above compounds seem to be endowed with a high therapeutic index: in fact, the acute toxicity values are several orders of magnitude higher than those used to achieve pharmacologically active doses. In the dosages and methodologies used and explained in the above experiments, administration to animals led to no mortalities, either long or short term, nor to any apparent signs of toxic effects.

The examples reported for the anti-platelet aggregation, antinflammatory and broncholytic properties, compared to substances of known activity, testify to the therapeutic interest of the pharmaceutical composition according to the invention.

I claim:

1. Ester derivatives of 7-(ω-oxyalkyl)theophylline of general formula

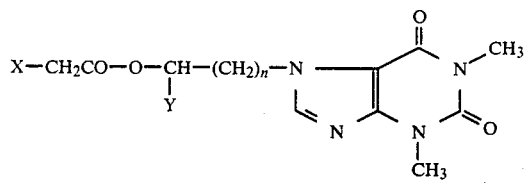

in which X represents an aroylpyrrol radical of formula

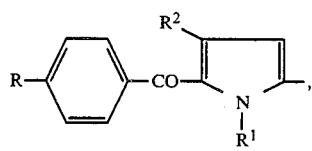

a pyrrylphenyl radical of formula

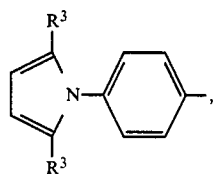

or an aroylpyrrolacetamide radical of formula

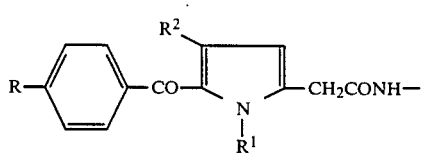

in which R is hydrogen, chloro, methyl or ethyl, $R^1$ is methyl or ethyl, $R^2$ is hydrogen or methyl, $R^3$ is hydrogen or methyl, Y represents hydrogen or the radical

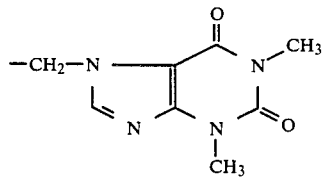

an n represents and integer between 1 and 5.

2. Compound according to claim 1, of formula

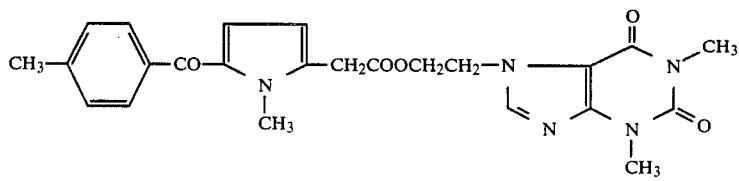

3. Compound according to claim 1, of formula

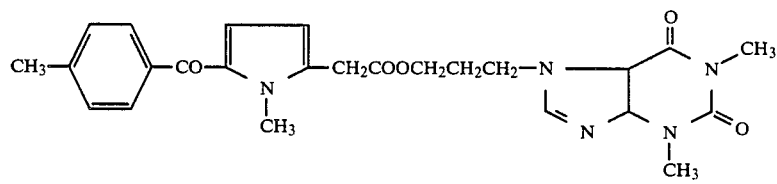

4. Compound according to claim 1, of formula

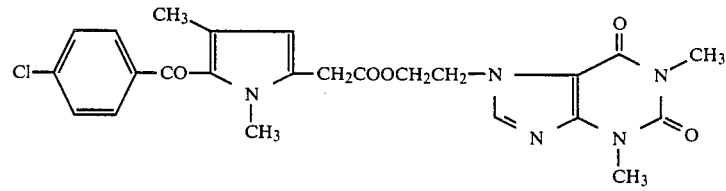

5. Compound according to claim 1, of formula

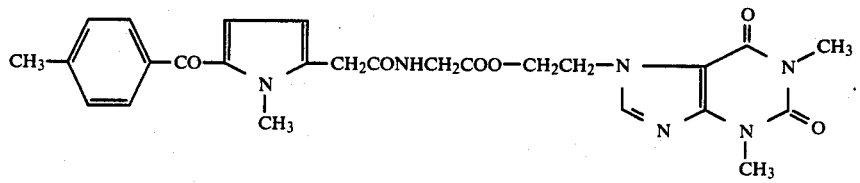

6. Compound according to claim 1, of formula

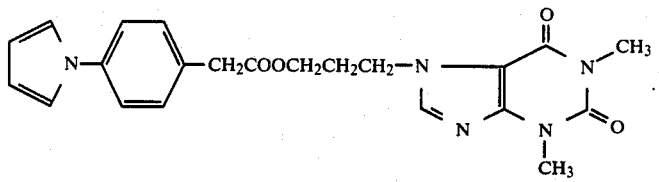

7. Compound according to claim 1, of formula

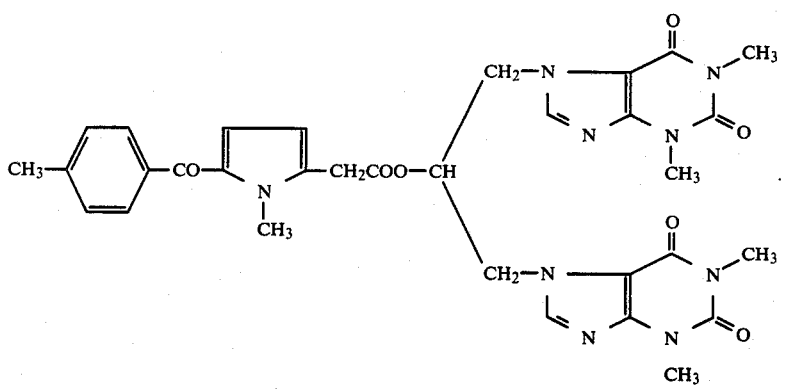

8. A compound according to claim 1 wherein Y is hydrogen.

9. Pharmaceutical composition comprising as an antiplatelet aggregation, antinflammatory and broncholytic agent a therapeutically effective quantity of a compound as defined in claim 1, in combination with a diluent or excipient.

10. A pharmaceutical composition according to claim 9 wherein Y is hydrogen.

11. A method for treating platelet aggregation in mammals comprising administering an effective amount of a compound as defined in claim 1, as an antiplatelet aggregant.

12. A method according to claim 11 wherein Y is hydrogen.

13. A process for the preparation of a compound as recited in claim 1 of the formula:

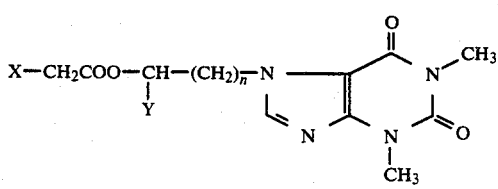

comprising reacting an alcohol of formula:

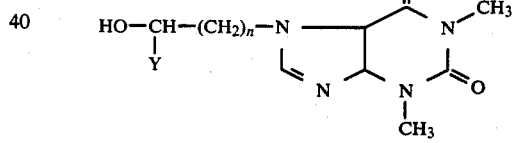

with 1-[5-(p-methylbenzoyl)-1-methyl-pyrrol-2-acetyl-]imidazole of formula:

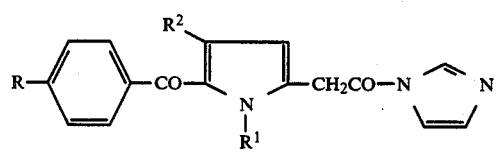

wherein X, Y, n, R, $R^1$, and $R^2$ have the same meaning as indicated in claim 1, in an inert solvent at a temperature between 60° and 90° C.

14. A process according to claim 13 where Y is hydrogen.

15. Process according to claim 13 wherein the reaction is run in the presence of catalyst selected from the group consisting of ethyl sodium and ethyl magnesium.

* * * * *